US008936800B2

(12) United States Patent
Orsoni et al.

(10) Patent No.: US 8,936,800 B2
(45) Date of Patent: *Jan. 20, 2015

(54) GEL COMPOSITION FOR TREATMENT OF COMMON ACNE COMPRISING A COMBINATION OF BENZOYL PEROXIDE AND ADAPALENE AND/OR ADAPALENE SALT

(71) Applicant: Galderma Research & Development, Biot (FR)

(72) Inventors: Sandrine Orsoni, Mandelieu (FR); Nathalie Willcox, Le Rouret (FR)

(73) Assignee: Galderma Research & Development, Biot (FR)

( * ) Notice: Subject to any disclaimer, the term of this patent is extended or adjusted under 35 U.S.C. 154(b) by 39 days.

This patent is subject to a terminal disclaimer.

(21) Appl. No.: 13/660,831

(22) Filed: Oct. 25, 2012

(65) Prior Publication Data

US 2013/0046022 A1    Feb. 21, 2013

Related U.S. Application Data

(63) Continuation of application No. 12/076,860, filed on Mar. 24, 2008, which is a continuation of application No. 10/326,389, filed on Dec. 23, 2002, now Pat. No. 7,820,186.

(60) Provisional application No. 60/351,382, filed on Jan. 28, 2002.

(30) Foreign Application Priority Data

Dec. 21, 2001  (FR) ..................... 01 16747

(51) Int. Cl.
| | | |
|---|---|---|
| A61K 8/00 | (2006.01) | |
| A61K 31/07 | (2006.01) | |
| A61K 31/075 | (2006.01) | |
| A61K 31/192 | (2006.01) | |
| A61K 31/327 | (2006.01) | |
| A61K 47/30 | (2006.01) | |
| A61K 31/20 | (2006.01) | |
| A61K 31/19 | (2006.01) | |

(52) U.S. Cl.
CPC .............. *A61K 31/20* (2013.01); *A61K 31/07* (2013.01); *A61K 31/19* (2013.01)
USPC ............ 424/401; 514/717; 514/725; 514/772

(58) Field of Classification Search
USPC ...................................................... 424/401
See application file for complete search history.

(56) References Cited

U.S. PATENT DOCUMENTS

| | | |
|---|---|---|
| 3,535,422 A | 10/1970 | Cox et al. |
| 4,056,611 A | 11/1977 | Young |
| 4,189,501 A | 2/1980 | Fulton |
| 4,355,028 A | 10/1982 | Kligman et al. |
| 4,717,720 A | 1/1988 | Shroot et al. |
| 4,792,452 A | 12/1988 | Howard et al. |
| 4,960,772 A | 10/1990 | Sebag et al. |
| 5,035,890 A | 7/1991 | Braun |
| RE34,440 E | 11/1993 | Shroot et al. |
| RE34,805 E | 12/1994 | Shroot et al. |
| 5,470,884 A | 11/1995 | Corless et al. |
| 5,607,980 A | 3/1997 | McAtee et al. |
| 5,648,389 A | 7/1997 | Gans et al. |
| 5,690,946 A | 11/1997 | Koulbanis et al. |
| 5,707,635 A | 1/1998 | Deckner et al. |
| 5,733,886 A | 3/1998 | Baroody et al. |
| 5,824,650 A | 10/1998 | De Lacharriere et al. |
| 5,968,528 A | 10/1999 | Deckner et al. |
| 5,976,513 A | 11/1999 | Robinson |
| 5,989,568 A | 11/1999 | Breton et al. |
| 6,106,848 A | 8/2000 | Preuilh et al. |
| 6,274,151 B1 | 8/2001 | Michel et al. |
| 6,423,324 B1 | 7/2002 | Murphy et al. |
| 6,444,647 B1 | 9/2002 | Robinson et al. |
| 6,559,189 B2 | 5/2003 | Baker et al. |
| 6,967,023 B1 | 11/2005 | Eini et al. |

(Continued)

FOREIGN PATENT DOCUMENTS

| | | |
|---|---|---|
| CN | 1072843 | 10/1992 |
| DE | 2801924 A | 7/1978 |

(Continued)

OTHER PUBLICATIONS

Advisory Action dated Aug. 27, 2012, in U.S. Appl. No. 13/110,814.
Advisory Action dated Oct. 28, 2010, in co-pending U.S. Appl. No. 11/826,364.
Bershard, V., "The Modern Age of Acne Therapy: A Review of Current Treatment Options," Mt. Sinai J. Med 2001, Sep.-Oct.; 68(4-5); 279-86.
Bikowski, "Clinical Experience Results with Clindamycin 1% Benzoyl Peroxide 5% Gel (Duac) as Monotherapy and in Combination", Journal of Drugs in Dermatology, Mar. 2005, pp. 164-171, vol. 4, No. 2.
Brand et al., "Cumulative Irritancy Comparison of Adapalene Gel 0,1% Versus Other Retinoid Products when Applied in Combination with Topical Antimicrobial Agents," J. Am. Acad. Dermatol., Sep. 2003, pp. S227-S232, vol. 49, No. 3, Cranbury, NJ.

(Continued)

*Primary Examiner* — Lakshmi Channavajjala
(74) *Attorney, Agent, or Firm* — Finnegan, Henderson, Farabow, Garrett & Dunner

(57) ABSTRACT

Dermatological/cosmetic compositions suited for preventing or treating cell differentiation and/or proliferation and/or keratinization disorders, including preventing or treating common acne, comprise, in a physiologically acceptable medium, (i) at least one dispersed retinoid, (ii) dispersed benzoyl peroxide, in free or encapsulated form, and (iii) at least one pH-independent gelling agent, selected from the group consisting of (a) polyacrylamide gelling agents, (b) gelling agents which are acrylic polymers coupled to hydrophobic chains, (c) modified starch gelling agents, and mixture thereof, said composition maintaining good chemical stability of (i) and (ii) without their degradation over time at a temperature of between 4° C. and 40° C.

3 Claims, No Drawings

(56) References Cited

U.S. PATENT DOCUMENTS

| | | | |
|---|---|---|---|
| 7,060,732 B2 | 6/2006 | Vishnupad et al. |
| 7,642,288 B2 | 1/2010 | Graeber |
| 7,820,186 B2 | 10/2010 | Orsoni et al. |
| 7,964,202 B2 | 6/2011 | Orsoni et al. |
| 8,071,644 B2 | 12/2011 | Abou-Chacra Vernet et al. |
| 8,080,537 B2 | 12/2011 | Abou-Chacra Vernet et al. |
| 8,105,618 B2 | 1/2012 | Orsoni-Segona et al. |
| 8,129,362 B2 | 3/2012 | Chacra Vernet et al. |
| 8,241,649 B2 | 8/2012 | Orsoni et al. |
| 8,445,543 B2 | 5/2013 | Abou-Chacra Vernet et al. |
| 2001/0051686 A1 | 12/2001 | Tabacchi et al. |
| 2002/0006906 A1 | 1/2002 | Stoltz et al. |
| 2002/0035161 A1 | 3/2002 | Segura et al. |
| 2002/0064541 A1 | 5/2002 | Lapidot et al. |
| 2002/0151527 A1 | 10/2002 | Wiegand et al. |
| 2003/0033678 A1 | 2/2003 | Schulze zur Wiesche et al. |
| 2003/0096012 A1 | 5/2003 | Besse et al. |
| 2003/0170196 A1 | 9/2003 | Orsoni et al. |
| 2004/0157766 A1 | 8/2004 | Embil et al. |
| 2004/0161402 A1 | 8/2004 | Brooks et al. |
| 2005/0148495 A1 | 7/2005 | Lambert et al. |
| 2005/0181999 A1 | 8/2005 | Ferrandis et al. |
| 2005/0238612 A1 | 10/2005 | Courcoux et al. |
| 2005/0239043 A1 | 10/2005 | Harding |
| 2005/0239723 A1 | 10/2005 | Amin et al. |
| 2006/0128808 A1 | 6/2006 | Arsonnaud et al. |
| 2006/0233735 A1 | 10/2006 | Preuith et al. |
| 2006/0234981 A1 | 10/2006 | Baker et al. |
| 2008/0176954 A1 | 7/2008 | Orsoni et al. |
| 2008/0181963 A1 | 7/2008 | Orsoni et al. |
| 2009/0191245 A1 | 7/2009 | Fredon et al. |
| 2009/0318550 A1 | 12/2009 | Mallard et al. |
| 2010/0022642 A1 | 1/2010 | Louis et al. |
| 2010/0029762 A1 | 2/2010 | Graeber et al. |
| 2010/0166852 A1 | 7/2010 | Mallard et al. |
| 2011/0135584 A1 | 6/2011 | Mallard |
| 2011/0318396 A1 | 12/2011 | Louis et al. |
| 2012/0059063 A1 | 3/2012 | Abou-Chacra Vernet et al. |
| 2012/0115947 A1 | 5/2012 | Abou-Chacra Vernet et al. |
| 2012/0136059 A1 | 5/2012 | Abou-Chacra Vernet et al. |

FOREIGN PATENT DOCUMENTS

| | | |
|---|---|---|
| EP | 0 335 115 | 10/1989 |
| EP | 1 458 369 | 12/2006 |
| EP | 1 967 180 | 9/2008 |
| FR | 2 225 167 | 11/1974 |
| FR | 2 378 523 | 8/1978 |
| FR | 2 618 673 | 2/1989 |
| FR | 2 628 319 | 9/1989 |
| FR | 2 687 312 | 8/1993 |
| FR | 2 753 626 | 3/1998 |
| FR | 2 833 841 | 6/2003 |
| GB | 1 594 314 | 7/1981 |
| GB | 2 130 486 | 6/1984 |
| GB | 2 207 353 | 2/1989 |
| GB | 2 088 717 | 3/1998 |
| HU | 218592 | 6/1996 |
| HU | 218936 | 2/1997 |
| JP | 1-100134 | 4/1989 |
| JP | 1-268632 | 10/1989 |
| JP | 7-500593 | 1/1995 |
| JP | 4889922 | 3/2012 |
| WO | WO 81/00206 | 2/1981 |
| WO | WO 93/07856 | 4/1993 |
| WO | WO 93/20796 | 10/1993 |
| WO | WO 95/31978 | 11/1995 |
| WO | WO 97/15282 | 1/1997 |
| WO | WO 99/44586 | 9/1999 |
| WO | WO 99/65456 | 12/1999 |
| WO | WO 00/37027 | 6/2000 |
| WO | WO 01/45647 | 6/2001 |
| WO | WO 01/45657 | 6/2001 |
| WO | WO 03/055472 | 7/2003 |
| WO | WO 2006/045640 | 5/2006 |
| WO | WO 2006/079563 | 8/2006 |
| WO | WO 2006/099192 | 9/2006 |
| WO | WO 2007/002831 | 1/2007 |
| WO | WO 2007/031883 | 3/2007 |
| WO | WO 2007/092312 | 8/2007 |
| WO | WO 2007/132134 | 11/2007 |
| WO | WO 2008/006848 | 1/2008 |
| WO | WO 2008/006888 | 1/2008 |
| WO | WO 2008/017914 | 2/2008 |
| WO | WO 2008/065306 | 6/2008 |
| WO | WO 2008/087354 | 7/2008 |

OTHER PUBLICATIONS

Capizzi et al., "Skin tolerability and efficacy of combustion therapy with hydrogen peroxide stabilized cream and adapalene gel in comparison with benzoyl peroxide cream and adapalene gel in common acne. A randomized, investigator-masked, controlled trial", British Journal of Dermatology, 2004, pp. 481-484, vol. 151, No. 2.

Capizzi, et al., "Efficacy and Safety of Combination Therapy of Hydrogen Peroxide Cream and Adapalene Gel in Comparison with Benzoyl Peroxide Cream and Adapalene in Common Acne," Journal of the American Academy of Dermatology, vol. 50, Issue 3, Supplement 1, p. P18 (Mar. 2004).

Caron et al., "Skin Tolerance of Adapalene 0.1% Gel in Combination with other Topical Antiacne Treatments", Journal of the American Academy of Dermatology, vol. 35, No. 6, Part 2, 1997, pp. S113-S115.

Chellquist et al., "Benzoyl Peroxide Solubility and Stability in Hydric Solvents," Pharmaceutical Research, vol. 9, No. 10, 1992, pp. 1341-1346, published by Springer, The Netherlands.

Clucas et al., "Adapalene 0.1% gel has low skin irritation potential", Journal of the European Academy of Dermatology and Venereology, Sep. 1998, p. S275, vol. 11 Elsevier Science Publisher.

Co-pending U.S. Appl. No. 12/457,774, filed Jun. 22, 2009.
Co-pending U.S. Appl. No. 13/110,814, filed May 18, 2011.
Co-pending U.S. Appl. No. 12/788,865, filed May 27, 2010.
Co-pending U.S. Appl. No. 12/076,859, filed Mar. 24, 2008, now U.S. Patent No. 7,964,202, issued Jun. 21, 2011.
Co-pending U.S. Appl. No. 12/076,860, filed Mar. 24, 2008.
Co-pending U.S. Appl. No. 12/457,788, filed Jun. 22, 2009.
Co-pending U.S. Appl. No. 13/296,186, filed Nov. 14, 2011.
Co-pending U.S. Appl. No. 13/308,413, filed Nov. 30, 2011.
Co-pending U.S. Appl. No. 13/351,986, filed Jan. 17, 2012.
Co-pending U.S. Appl. No. 12/884,684, filed Sep. 17, 2010, now U.S. Patent No. 8,105,618, issued Jan. 31, 2012.
Co-pending U.S. Appl. No. 13/103,613, filed May 9, 2011.
Co-pending U.S. Appl. No. 11/826,364, filed Jul. 13, 2007, now U.S. Patent No. 8,129,362, issued Mar. 6, 2012.
Co-pending U.S. Appl. No. 12/318,937, filed Jan. 13, 2009, continuation of Application No. PCT/EP2007/057207, filed on Jul. 12, 2007, now U.S. Patent No. Dec. 6, 2011.
Co-pending U.S. Appl. No. 12/473,981, filed May 28, 2009, continuation-in-part of U.S. Appl. No. 12/318,937, now U.S. Patent No. 8,080,537, issued Dec. 20, 2011.

Definition of "essential oil," The Condensed Chemical Dictionary, Tenth Edition, Ed. Gessner G. Hawley, Van Nostrand Reinhold Company, NY, NY, 1981, p. 418.

English language abstract of FR 2 687 312, Aug. 20, 1993.
English language abstract of DE 2802924 A, Jul. 1978.
English language abstract of FR 2 833 841, Jun. 27, 2003.
English language abstract of EP 1 967 180, Sep. 2008.

FDA label for Differin 0.1% gel NDA No. 020380 (3 pages), Apr. 2007.

French Search Report for FR 01/16747, dated Sep. 4, 2002.

Gollnick et al., "Evaluation of a maintenance treatment of acne vulgaris with adapalen gel 0.1%", Journal of the American Academy of Dermatology, Mar. 2005, p. P18, vol. 52, No. 3.

Hercules, "Product Data: Nastrosol® 250 Water Soluable Hydroxyethylcellulose," 2005, Aqualon, Accessed Online Nov. 1, 2010, http://www.in-cosmetics.com/ExhibitorLibrary/108/33015e11.pdf.

(56) References Cited

OTHER PUBLICATIONS

Hurwitz, "The Combined Effect of Vitamin A Acid and Benzoyl Peroxide in the Treatment of Acne," vol. 17, No. 3, Mar. 1976, pp. 585-590.
International Search Report for EP 02799797, dated Mar. 24, 2003.
International Search Report for PCT/EP2007/057207, dated Sep. 24, 2007.
International Search Report for PCT/FR2007/052606, dated Sep. 16, 2008.
International Search Report for PCT/FR/2008/052169. dated Sep. 22, 2009.
Korkut et al., "Benzoyl Peroxide, Adapalene, and their Combination in the Treatment of Acne Vulgaris", The Journal of Dermatology, 2005, pp. 169-173, vol. 32, No. 3, Edirne, Turkey.
Leyden, et al., "Photographic Review of Results From a Clinical Study Comparing Benzoyl Peroxide 5%/Clindamycin 1% Topical Gel with Vehicle in the Treatment of Rosacea," Topical Treatment for the Inflamed Lesion in Acne, Rosacea, and Pseudofolliculitis Barbee, Jun. 2004, vol. 73, p. 3.
Leyden, James J., "A Review of the Use of Combination Therapies for the Treatment of Acne Vulgaris," Journal of the American Academy of Dermatology, vol. 49, No. 3, pp. S200-S210 (Sep. 2003).
Martin et al. "Chemical Stability of Adapalene and Tretinoin when Combined with Benzoyl Peroxide in Presence and in Absence of Visible Light and Ultraviolet Radiation," British Journal of Dermatology, vol. 139, No. S52, 1998, pp. 8-11.
Michalun et al., "Milady's Skin Care and Cosmetic Ingredients Dictionary," 1994, p. 175, Milady Publishing Company, Albany, NY, ISBN: 1-56253-125-5.
Millikan, "Adapalene: an update on newer comparative studies between the various retinoids," 2000, Int'l Journal of Dermatology, 39: 784-788.
Mills Jr. et al., Comparing 2.5%, 5% and 10% benzoyl peroxide on inflammatory acne vulgaris. Int. J. Dermatology, Dec. 1986; 25(10); 664-667.
Notice of Allowance dated Aug. 5, 2011, in co-pending U.S. Appl. No. 12/318,937, now U.S. Patent No. 8,071,644.
Notice of Allowance dated Jun. 4, 2012, in co-pending U.S. Appl. No. 13/103,613.
Notice of Allowance dated Sep. 9, 2010, in parent U.S. Appl. No. 10/326,389, now U.S. Patent No. 7,820,186.
Notice of Allowance mailed Feb. 22, 2011, in U.S. Appl. No. 12/076,859, now U.S. Patent No. 7,964,202.
Notice of Allowance dated Sep. 6, 2011, in U.S. Appl. No. 12/473,981, now U.S. Patent No. 8,080,537.
Notice of Allowance dated Oct. 18, 2011, in U.S. Appl. No. 11/826,364, now U.S, Patent No. 8,129,362.
Notice of Allowance dated Feb. 1, 2011, in U.S. Appl. No. 11/826,364, now U.S. Patent No. 8,129,362.
Notice of Allowance dated Oct. 31, 2011, in U.S. Appl. No. 12/884,684, now U.S. Patent No. 8,105,618.
Office Action dated May 24, 2012, in U.S. Appl. No. 12/788,865.
Office Action dated Dec. 23, 2011, in U.S. Appl. No. 12/788,865.
Office Action dated May 21, 2012, in U.S. Appl. No. 13/110,814.
Office Action dated Jan. 13, 2012, in U.S. Appl. No. 13/110,814.
Office Action dated Jun. 5, 2012, in U.S. Appl. No. 12/457,774.
Office Action dated Oct. 12, 2012, in U.S. Appl. No. 13/351,986.
Office Action dated Aug. 9, 2012, in U.S. Appl. No. 13/308,413.
Office Action dated Sep. 20, 2012, in U.S. Appl. No. 13/296,186.
Office Action dated Sep. 7, 2012, in U.S. Appl. No. 12/076,860.
Office Action mailed Apr. 5, 2012, in U.S. Appl. No. 12/076,860.
Office Action mailed Sep. 9, 2011, in U.S. Appl. No. 12/884,684, now U.S. Patent No. 8,105,618.
Office Action dated Aug. 17, 2010, in parent U.S. Appl. No. 10/326,389, now U.S. Patent No. 7,820,186.
Office Action dated Aug. 3, 2007, in parent U.S. Appl. No. 10/326,389, now U.S. Patent No. 7,820,186.
Office Action dated Dec. 29, 2009, in U.S. Appl. No. 11/826,364, now U.S. Patent No. 8,129,362.
Office Action dated Dec. 8, 2010, in U.S. Appl. No. 12/076,859, now U.S. Patent No. 7,964,202.
Office Action dated Feb. 1, 2010, in parent U.S. Appl. No. 10/326,389, now U.S. Patent No. 7,820,186.
Office Action dated Feb. 15, 2011, in U.S. Appl. No. 12/076,860.
Office Action dated Jul. 23, 2010, in U.S. Appl. No. 11/826,364, now U.S. Patent No. 8,129,362.
Office Action dated Jun. 11, 2009, in parent U.S. Appl. No. 10/326,389, now U.S. Patent No. 7,820,186.
Office Action dated Jun. 17, 2011, in U.S. Appl. No. 12/076,860.
Office Action dated May 15, 2008, in parent U.S. Appl. No. 10/326,389, now U.S. Patent No. 7,820,186.
Office Action dated Nov. 17, 2006, in parent U.S. Appl. No. 10/326,389, now U.S. Patent No. 7,820,186.
Office Action dated Nov. 17, 2008, in parent U.S. Appl. No. 10/326,389, now U.S. Patent No. 7,820,186.
Office Action dated Oct. 21, 2009, in U.S. Appl. No. 12/318,937, now U.S. Patent No. 8,071,644.
Office Action dated Sep. 1, 2010, in U.S. Appl. No. 12/318,937, now U.S. Patent No. 8,071,644.
Office Action dated Sep. 3, 2010, in U.S. Appl. No. 12/473,981, now U.S. Patent No. 8,080,537.
Office Action dated Sep. 30, 2005, in parent U.S. Appl. No. 10/326,389, now U.S. Patent No. 7,820,186.
Office Action mailed Jul. 18, 2011, in U.S. Appl. No. 12/457,788.
Office Action mailed Mar. 16, 2012, in U.S. Appl. No. 12/457,788.
Office Action mailed Mar. 25, 2011, in U.S. Appl. No. 12/473,981, now U.S. Patent No. 8,080,537.
Office Action mailed Mar. 3, 2011, in U.S. Appl. No. 12/318,937, now U.S. Patent No. 8,071,644.
Office Action mailed May 31, 2012, in U.S. Appl. No. 13/351,986.
Pongjanyakul et al., "Influence of magnesium aluminum silicate on rheological, release, and permeation characteristics of diclofenac sodium aqueous gels in vitro," Apr. 2005, J. Pharm. Pharmacol., 57(4):429-34, PubMed abstract; PMID: 15831202.
Related U.S. Appl. No. 10/326,389, filed Dec. 23, 2002, now U.S. Patent No. 7,820,186, issued Oct. 26, 2010.
Relyveld et al., "Benzoyl peroxide/clindamycin/UVA is more effective than fluticasone/UVA in progressive macular hypomelanosis: A randomized study,"J. Am. Acad. Dermatol., Nov. 2006.
Seppic, Personal Care Ingredients Catalog, pp. 1-26 and endnotes, 2004/rev. 2006, published by Seppic S.A., Lyon France.
Thiboutot et al., Adapalene-benzoyl peroxide, a fixed-dose combination for the treatment of acne vulgaris: results of a multicenter, randomized double-blind, controlled study, Nov. 2007.
*Uniloc USA, Inc.* v. *Microsoft Corp.*, 632 F. 3d 1292 (Fed. Cir. 2011).
Van Zuuren, et al., "Systematic review of rosacea treatments," J. Am. Acad. Dermatol., Jan. 2007, vol. 56, No. 1, pp. 107-115.
Walker, Susan J., M.D., "Summary Review" dated Dec. 1, 2008. NDA No. 22-320 (6 pages).
Weiss et al., "Adapalene for the treatment of acne vulgaris", Journal of the American Academy of Dermatology, Aug. 1998, pp. S50-S54, vol. 39, No. 2.
Wen-Wen et al., "Clinical efficacy and safety of 5% benzoyl peroxide gel combined with 0.1% adapalene gel in the treatment of acne vulgaris: a multicenter randomized study", Database Biosis, Biosciences Information Service, Jun. 2003, Database accessionno. PREV200300514701, pp. 310-312, vol. 36, No. 6.
BenzaClin™ Topical Gel, Final Printed Labeling, Center for Drug Evaluation and Research, Application No. 50-756, Dec. 21, 2000.
Berson, D., "Using the Newest Topical Agents for Treating Acne," Acne & Rosacea: Current Trends in Diagnosis and Treatment, Supplement to Skin & Aging. Oct. 1999, pp. 6-9.
Berson et al. "The treatment of acne: The role of combination therapies," *J. Am. Acad. Dermatol.*, May 1995, pp. S31-S41.
Brogden et al., "Adapalene: A Review of its Pharmacological Properties and Clinical Potential in the Management of Mild to Moderate Acne," Drugs Mar. 1997; 53 (3), pp. 511-519.
Clindoxyl Gel (clindamycin, 1%—benzoyl peroxide, 5%), Medical Reviews, Center for Drug Evaluation and Research. Application No. 05-741, Aug. 15, 2000.
Co-pending U.S. Appl. No. 13/892,392, filed May 13, 2013.
Co-pending U.S. Appl. No. 12/458,982, filed Jul. 29, 2009.

(56) References Cited

OTHER PUBLICATIONS

Co-pending U.S. Appl. No. 12/318,938, filed Jan. 13, 2009.
Cunliffe et al., Clinical efficacy and safety comparison of adapalene gel and tretinoin gel in the treatment of acne vulgaris: Europe and U.S. multicenter trials, *J. Am. Acad. Dermatol.*, vol. 35, No. 6, Part 2, pp. S126-S134 (1997).
Differin-Adapalene Data Sheet, product insert as of Nov. 1996, pp. 1-5.
Draft Guidance for Industry: Acne Vulgaris, Developing Drugs for Treatment, U.S. Dept. HHS, FDA, Center for Drug Evaluation and Research, Sep. 2005, pp. 1-14.
Duac Topical Gel (clindamycin, 1%—benzoyl peroxide, 5%), Final Printed Labeling, Center for Drug Evaluation and Research, Application No. 50-741, Aug. 15, 2000.
Ellis et al., "Comparison of adapalene 0.1% solution and tretinoin 0.025% gel in the topical treatment of acne vulgaris," *Br. J. Dermatol.* (1998) 139 (Supp. 52), pp. 41-47.
Hurwitz, S., "The Combined Effect of Vitamin A Acid and Benzoyl Peroxide in the Treatment of Acne," *Cutis*, vol. 17, No. 8, Mar. 1976, pp. 585-590.
International Search Report for PCT/EP2008/051155, dated Jun. 26, 2008.
Leyden et al., "Comparison of Treatment of Acne Vulgaris with Alternative-Day Appiications of Tazarotene 0.1% Gel and Once-Daily Applications of Adapalene. 0.1% Gel: A Randomized Trial," *Cutis*, Jun. 2001, pp. 10-16, vol. 67.
Lucky et al., "Efficacy and Tolerance of Adapalene Cream 0.1% Compared with Its Cream Vehicle for the Treatment of Acne Vulgaris," *Cutis*, vol. 68, Oct. 2001, pp. 34-40.
Millikan, L. E., "Pivotal clinical trials of adapalene in the treatment of acne," *Eur. Acad. Dermatol. and Venereology JEADV*, (2001) 15 (Supp. 3), pp. 19-22.
Notice of Abandonment dated Jul. 27, 2011, in U.S. Appl. No. 12/318,938.
Notice of Allowance dated Dec. 26, 2012, in U.S. Appl. No. 13/660,831.
Office Action dated Sep. 19, 2011, in U.S. Appl. No. 12/458,982.
Office Action dated Nov. 18, 2010, in U.S. Appl. No. 12/318,938.
Office Action dated Jun. 10, 2013, in U.S. Appl. No. 13/351,986.
Physicians' Desk Reference, 2003, 57$^{th}$ Edition, pp. 1381-1382, Differing® (adapalene gel).
Report on the Filing or Determination of an Action Regarding a Patent or Trademark, filed in U.S. Patent Nos. 7,520,186, 7,964,202, 8,071,644, 8,080,537, 8,105,618, and 8,129,362, on Jul. 18, 2012.
Report on the Filing or Determination of an Action Regarding a Patent or Trademark, filed in U.S. Patent Nos. 8,071,644, 8,050,537, and 8,129,362, on Sep. 10, 2012.
Report on the Filing or Determination of an Action Regarding a Patent or Trademark dated Oct. 1, 2012.
Report on the Filing or Determination of an Action Regarding a Patent or Trademark, filed in U.S. Patent Nos. 8,071,644, 8,080,537, and 8,129,362, on Jul. 25, 2013.
Report on the Filing or Determination of an Action Regarding a Patent or Trademark dated Sep. 16, 2013.
Shalita et al,, "A comparison of the efficacy and safety of adapalene gel 0.1% and tretinoin gel 0.025% in the treatment of acne vulgaris: A multicenter trial," *J. Am. Acad. Dermatol.*, 1996, vol. 34, No. 3, pp. 482-485.
Usatine, R., "Med.Pix: The science and art of treating acne in adolescence," *West J. Med.*, Mar. 2000, vol. 172, pp. 155-156.
Zaenglein et al., "Expert Committee Recommendations for Acne Management,"*Pediatrics*, vol. 118, No. 3, Sep. 2006, pp. 1188-1199.
Zousoulis et al , "A multicentre, single-blind, randomized comparison of a fixed clindamycin phosphate/tretinoin gel formulation (Velac®) applied once daily and a clindamycin lotion formulation (Dalacin T®) applied twice daily in the topical treatment of acne vulgaris," *Br. J. Dermatol.*, vol. 143, pp. 498-505 (2000).
Extended European Search Report issued Mar. 30, 2012, in European Patent Application No. 12 152 317, Written Opinion and originally filed claims 1-10 of EP 12 152 317 (14 pages).

LV do Nascimento et al., "Single-blind comparative clinical study of the efficacy and safety of benzoyl peroxide 4% gel (BID) and adapalene 0.1% Gel (QD) in the treatment of acne vulgaris for 11 weeks," Journal of Dermatological Treatment, 2003, pp. 166-171, vol. 14.
Notice of Allowance dated Feb. 8, 2013, in U.S. Appl. No. 13/308,413.
Office Action dated Aug. 2, 2012, in U.S. Appl. No. 13/308,413.
Physicians' Desk Reference, U.S.A., Medical Economics Company, Inc., 2000, 54 Edition, pp. 1, 731-732.
Physicians' Desk Reference, U.S.A., Medical Economics Company, Inc., 2000, 54 Edition, pp. 932, "Benzagel®" section.
Physicians' Desk Reference, U.S.A., Medical Economics Company, Inc., 2000, 54 Edition, pp. 1, 102-103, "Benza AC®" section.
Physicians' Desk Reference, U.S.A., Medical Economics Company, Inc., 2000, 54 Edition, pp. 1, 104-105, "Differin®" section.
41506: New Composition, Research Disclosure, No. 415, p. 1424 (1998).
41640: Phosphoric Diester of Vitamin C and of Vitamin E, Research Disclosure, No. 418 pp. 206-208 (1999).
41847: Polyphenols Extracted From Red Wine, Research Disclosure, No. 418, pp. 212-214 (1999).
Benzaclin Topical Gel Product, packaging and insert (Aug. 2012).
Benzamycin® Gel Product, packaging and insert (Aug. 2012).
Brevoxyl®-4 Gel Product, packaging and insert (Revised 2010).
Desquam-X® 5 or 10 Wash, packaging and insert (Revised Nov. 2009).
Differin® Cream Product, packaging and prescribing information (Nov. 2009).
Differin® Gel Product 0.1%, packaging and prescribing information (Sep. 2003).
Differin® Gel Product 0.3%, packaging and prescribing information (Mar. 2012).
Differin® Cream Product 0.1%, packaging and prescribing information (Nov. 2011).
Duac Topical Gel Product, packaging and prescribing information (Jan. 2014).
Elmore, "Final Report on the Safety Assessment of Aluminum Silicate, Calcium Silicate, Magnesium Aluminum Silicate, Magnesium Silicate, Magnesium Trisilicate, Sodium Magnesium Silicate, Zirconium Silicate, Attapulgite, Bentonite, Fuller's Earth . . . ", 2003, Int'l Journal of Toxicology, 22(Suppl. 1):37-102.
G. Plewig et al., "Kinetics of Epidermis and Adnexa Following Vitamin A Acid in the Human," *Acta Dermatovener* (Stockholm), suppl. 74, pp. 87-98 (1975).
H. Gollnick, "Current Concepts of the Pathogenesis of Acne," Drugs, vol. 63, pp. 1579-1596 (2003).
I. Handojo, "Retinole Acid Cream (Airol Cream) and Benzoyl-Peroxide in the Treatment of Acne Vulgaris," Southeast Asian J. Tropical Med. And Pub. Health, vol. 10, pp. 548-551 (1979).
J.E. Wolf, Jr., et al, "Efficacy and Tolerability of Combined Topical Treatment of Acne Vulgaris with Adapalene and Clindamycin: a multicenter, Randomized, Investigator-blinded Study," J. Am. Acad. Dermatology, vol. 49, Suppl., pp. S211-S217 (2003).
L. Fang et al., "Efficacy and Safety of Benzoyl Peroxide Gel, 5% Combined with Adapalene Gel, 0.1% in Chinese Patients With Acne Vulgaris," Dermatologie, 20th World Congress of Derematology, Jul. 1-5, 2002, Paris, P0020 (2002).
M. Verschoore et al, "Efficacy and Safety of CD 271 Alcoholic Gels in the Topical Treatment of Acne Vulgaris," Br. J. Dermatdogy vol. 124, pp. 368-371 (1991).
Mills et al., "Assay of Comedolytic Activity in Acne Patients," Acta Derm. Venereol., 1983, 63(1) pp. 68-71, Stockholm.
Mills et al., "A human model for assaying comedolytic substances," British Journal of Dermatology, 1982, vol. 107, pp. 543-548, British Association of Dermatologists, UK.
Office Action dated Dec. 23, 2013, in U.S. Appl. No. 12/457,788.
Office Action dated Dec. 5, 2013, in U.S. Appl. No. 13/110,814.
Office Action dated Oct. 8, 2013, in U.S. Appl. No. 12/788,865.
Office Action dated Oct. 10, 2013, in U.S. Appl. No. 12/458,982.
Office Action issued Sep. 25, 2012, by the Japanese Patent Office in corresponding Japanese Patent Application No. 2009-518901, and an

(56) References Cited

OTHER PUBLICATIONS

English language translation thereof (6 pages in Japanese and 6 pages in English) with an English language copy of the examined claims (3 pages).

Physician's Desk Reference (Medical Economics Co., 53rd ed. 1999).

Seppic, "Sepigel®-Simulgel® Formulator's Essential Partners" (Mar. 2001).

Tan et al., "Synergistic efficacy of adapalene 0.1%-benzoyl perioxide 2.5% in the treatment of 3855 acne vulgaris patients," Journal of Dermatological Treatment, 2010, Early Online, pp. 1-9, Informa UK Ltd., UK.

GEL COMPOSITION FOR TREATMENT OF COMMON ACNE COMPRISING A COMBINATION OF BENZOYL PEROXIDE AND ADAPALENE AND/OR ADAPALENE SALT

CROSS-REFERENCE TO EARLIER APPLICATIONS

This is a continuation of U.S. application Ser. No. 12/076,860, filed Mar. 24, 2008, as a continuation of U.S. application Ser. No. 10/326,389, filed Dec. 23, 2002, which claims the benefit under 35 U.S.C. §119 of French Patent Application No. 01 16747, filed Dec. 21, 2001, and the benefit of U.S. Provisional Application No. 60/351,382, filed Jan. 28, 2002.

BACKGROUND OF THE INVENTION

1. Technical Field of the Invention

The invention relates to a composition comprising, in a physiologically acceptable medium, at least one retinoid, dispersed benzoyl peroxide and at least one pH-independent gelling agent.

2. Description of the Prior Art

The use of several classes of active principles is a therapeutic tool that is frequently employed, especially for treating dermatological disorders.

Specifically, it is known practice in the treatment of dermatitis to use corticosteroids such as, for example, hydrocortisone, miconazole or betamethasone valerate, antihistamines (e.g., mizolastine) and/or keratolytic agents, for instance salicylic acid. Various antifungal agents, for instance allylamine derivatives, triazoles, antibacterial agents or antimicrobial agents such as, for example, antibiotics, quinolones and imidazoles, are also conventionally combined in the treatment of dermatological diseases. Peroxides, D vitamins and retinoids are also described for the topical treatment of various pathologies associated with the skin or mucous membranes, in particular acne.

The combination of several local treatments (antibiotics, retinoids, peroxides and zinc) is also used in dermatology to increase the efficacy of the active principles and to reduce their toxicity (Cunliffe W. J., *J. Dermatol, Treat.*, 2000, 11 (suppl2), pp. 13-14).

The multiple application of various dermatological products may be relatively burdensome and restricting for the patient.

The value in seeking to obtain a novel treatment that is effective on dermatological complaints in a stable composition offering good cosmetic utility, allowing a single application and a utilization that the patient finds pleasant, may thus be appreciated.

Among this panoply of treatments proposed to a person skilled in the art, there was nothing to encourage him to combine, in the same composition, benzoyl peroxide and a retinoid.

However, formulating such a composition poses several problems.

Firstly, the efficacy of benzoyl peroxide is associated with its decomposition when it is placed in contact with the skin. Specifically, it is the oxidizing properties of the free radicals produced during this decomposition that lead to the desired effect. Thus, in order to maintain the optimum efficacy of benzoyl peroxide, it is important to prevent its decomposition before use, i.e., during storage.

Benzoyl peroxide is an unstable chemical compound, making it difficult to formulate it in finished products.

The solubility and stability of benzoyl peroxide were studied by Chellquist at al., in ethanol, propylene glycol and various mixtures of polyethylene glycol 400 (PEG 400) and water (Chellquist E. M. and Gorman W. G., *Pharm. Res.*, 1992, Vol 9: 1341-1346). Benzoyl peroxide is particularly soluble in PEG 400 and ethanol, as shown in the following table:

| Solvent | Benzoyl peroxide solubility (mg/g) |
| --- | --- |
| PEG 400 | 39.6 |
| Ethanol | 17.9 |
| Propylene glycol | 2.95 |
| Propylene glycol/water (75:25) | 0.36 |
| Glycerol | 0.15 |
| Water | 0.000155 |

The said document moreover states that the stability of benzoyl peroxide is greatly influenced by the chemical composition of the formulation and by storage temperature. Benzoyl peroxide is extremely reactive and degrades in solution at low temperature on account of the instability of its peroxide bond. The authors thus state that benzoyl peroxide in solution degrades more or less quickly in all the solvents studied as a function of the type of solvent and of its concentration.

The degradation times for benzoyl peroxide in PEG 400 (0.5 mg/g), in ethanol and in propylene glycol are, respectively, 1.4, 29 and 53 days at 40° C.

Such a degradation does not allow the preparation of a product intended for sale.

It is moreover known that benzoyl peroxide is more stable in water and propylene glycol when it is in suspension (i.e., in dispersed form), since it is not degraded after storage for 90 days in these solvents. Thus, in order to limit the problem of rapid instability of benzoyl peroxide in solution, it has been found to be advantageous to formulate benzoyl peroxide in dispersed form. However, this type of formulation is not entirely satisfactory since degradation of the benzoyl peroxide in the finished product is still observed.

Another difficulty to be overcome in preparation of a composition comprising both benzoyl peroxide and a retinoid is that most retinoids are particularly sensitive to natural oxidation, to visible light and to ultraviolet light, and, since benzoyl peroxide is a strong oxidizing agent, the chemical compatibility of these compounds in the same formulation poses numerous problems in terms of physical and chemical stability.

A study of the stability of two retinoids was performed by combining two commercial products, one containing a retinoid (tretinoin or adapalene) and the second based on benzoyl peroxide (B. Martin et al., Br. *J. Dermatol.* (1998) 139, (suppl. 52), 8-11). The presence of the formulation based on benzoyl peroxide results in very rapid degradation of the oxidation-sensitive retinoids: it is measured that 50% of the tretinoin is degraded in 2 hours, and 95% in 24 hours. In the composition in which the retinoid is adapalene, no degradation of the adapalene was measured over 24 hours. This study confirms that benzoyl peroxide becomes degraded and degrades oxidation-sensitive retinoids over time, gradually releasing benzoic acid into the finished products. In contrast, no indication is given regarding the physical stability of the two compositions placed in contact, or regarding the therapeutic activity that may finally be obtained by combining the two active principles in the same composition. There was no encouragement for combining these two active agents in order to obtain a stable composition of gel type, given that it was commonly known that the presence of benzoyl peroxide chemically and physically destabilized this type of composition.

Now, it is clear that the degradation of benzoyl peroxide and retinoids is not desirable since it impairs the efficacy of the composition containing them.

Moreover, a finished product, in particular when it is a pharmaceutical or cosmetic composition, must maintain throughout its shelf life precise physicochemical criteria for ensuring its pharmaceutical or cosmetic quality, respectively. Among these criteria, it is necessary for the rheological properties to be maintained. They define the behavior and texture of the composition during application, but also the active principle's release properties [1998 SFSTP Commission Report] and the homogeneity of the product when the active principles are present therein in dispersed form.

In particular, the formulation of benzoyl peroxide and of a retinoid in gel form is advantageous for topical treatments, such as the treatment of acne, since it especially avoids a greasy feel being left on the skin.

Another difficulty to be overcome in preparing a composition especially comprising benzoyl peroxide, when it is in gel form, is that the gelling agents are destabilized by the benzoic acid released during the degradation of the benzoyl peroxide.

Specifically, the thickeners most commonly used for formulating these compositions with benzoyl peroxide are acrylic acid polymers (Carbomer) and celluloses alone or combined with silicates.

Now, the use of carbomers in compositions of aqueous gel type does not give good results in terms of chemical stability of the benzoyl peroxide or in terms of rheological stability. As described by Bollinger (Bollinger, Journal of Pharmaceutical Science, 1977, vol 5), it has been observed that from 5% to 20% benzoyl peroxide is lost after 2 months at 40° C. depending on the neutralizer of the carbomer used. Furthermore, the release of benzoic acid results in depolymerization of the carbomers, leading to a drop in viscosity which may result in phase separation. In other gels consisting of a mixture of hydroxypropyl-cellulose and aluminum magnesium silicate, a drop in viscosity over time is also observed, resulting in sedimentation of the active agents as a suspension and heterogeneity of the dispersion in the finished product.

This instability of benzoyl peroxide gels impairs their efficacy and their cosmetic utility.

There is thus still a need for a physically stable gelled composition containing benzoyl peroxide and a retinoid.

SUMMARY OF THE INVENTION

The Applicant has now, surprisingly, produced a composition that satisfies this need, which comprises dispersed, free or encapsulated benzoyl peroxide, at least one retinoid and a pH-independent gelling agent with good physical stability, i.e., not showing a drop in viscosity over time and at temperatures of between 4 and 40° C., and maintaining good chemical stability of the two active agents (benzoyl peroxide and retinoid), i.e., no degradation of the active agents over time and at temperature of between 4 and 40° C. is observed. The Applicant has also discovered, surprisingly, that total dispersion of the active principles can be obtained by following a particular preparation process. This preparation process performed without heat makes it possible to obtain an optimum particle size and uniform dispersion of the two active agents in the composition, while at the same time ensuring the physical stability of the product.

The invention thus relates to a composition comprising, in a physiologically acceptable medium, at least one retinoid, dispersed benzoyl peroxide and at least one pH-independent gelling agent.

DETAILED DESCRIPTION OF BEST MODE AND SPECIFIC/PREFERRED EMBODIMENTS OF THE INVENTION

The composition according to the invention is preferably in the form of an aqueous gel.

The term "aqueous gel" means a composition containing, in an aqueous phase, a viscoelastic mass formed from colloidal suspensions (gelling agent).

The expression "pH-independent gelling agent" means a gelling agent capable of giving the composition a viscosity that is sufficient to keep the retinoid and the benzoyl peroxide in suspension, even under the influence of a variation in pH caused by the release of benzoic acid by the benzoyl peroxide.

Non-limiting examples that may be mentioned include the gelling agents of the polyacrylamide family, such as the mixture of sodium acryloyldimethyltaurate copolymer/isohexadecane/polysorbate 80 sold under the name Simulgel 600 by the company SEPPIC, the mixture of polyacrylamide/isoparaffin C13-14/laureth-7 such as, for example, the product sold under the name Sepigel 305 by the company SEPPIC, the family of acrylic polymers coupled to hydrophobic chains, such as the PEG-150/decyl/SMDI copolymer sold under the name Aculyn 44 (polycondensate comprising at least, as components, a polyethylene glycol containing 150 or 180 mol of ethylene oxide, decyl alcohol and methylenebis (4-cyclohexyl isocyanate) (SMDI), at 35% by weight in a mixture of propylene glycol (39%) and water (26%)), the family of modified starches, such as the modified potato starch sold under the name methylenebis (4-cyclohexyl isocyanate) (SMDI), Structure Solanace, or mixtures thereof.

The preferred gelling agents are derived from the polyacrylamide family, such as Simulgel 600 or Sepigel 305, or mixtures thereof.

The gelling agent as described above may be used in preferential concentrations ranging from 0.1% to 15% and more preferably ranging from 0.5% to 5%.

The composition according to the invention contains at least one retinoid.

The term "retinoid" means any compound that binds to the RAR and/or RXR receptors.

Preferably, the retinoid is a compound chosen from the family of benzonaphthalene retinoids as described in patent application EP 0 199 636. In particular, adapalene and also precursors and/or derivatives thereof will be preferred.

The expression "retinoid precursors" means the immediate biological precursors or substrates thereof, and also the chemical precursors thereof.

The expression "retinoid derivative" means both their metabolic derivatives and their chemical derivatives.

Other retinoids may be chosen from those described in the following patents or patent applications: U.S. Pat. No. 4,666, 941, U.S. Pat. No. 4,581,380, EP 0 210 929, 15 EP 0 232 199, EP 0 260 162, EP 0 292 348, EP 0 325 540, EP 0 359 621, EP 0 409 728, EP 0 409 740, EP 0 552 282, EP 0 584 191, EP 0 514 264, EP 0 514 269, EP 0 661 260, EP 0 661 258, EP 0 658 553, EP 0 679 628, EP 0 679 631, EP 0 679 630, EP 0 708 100, EP 0 709 382, EP 0 722 928, EP 0 728 739, EP 0 732 328, EP 0 740 937, EP 0 776 885, EP 0 776 881, EP 0 823 903, EP 0 832 057, EP 0 832 081, EP 0 816 352, EP 0 826 657, EP 0 874 626, EP 0 934 295, EP 0 915 823, EP 0 882 033, EP 0 850 909, EP 0 879 814, EP 0 952 974, EP 0 905 118, EP 0 947 496, WO 98/56783, WO 99/10322, WO 99/50239, WO 99/65872.

Needless to say, the amount of the two active agents, benzoyl peroxide and retinoid, in the composition according to the invention will depend on the combination chosen and thus particularly on the retinoid under consideration and the quality of the desired treatment.

The preferred retinoid concentrations are between 0.0001% and 20% by weight relative to the total weight of the composition.

Benzoyl peroxide may also be used in free form or in an encapsulated form in a form adsorbed onto, or absorbed in, any porous support. It may be, for example, benzoyl peroxide encapsulated in a polymer system consisting of porous microspheres, such as, for example, microsponges sold under the name Microsponges P009A Benzoyl peroxide by the company Advanced Polymer System.

To give an order of magnitude, the composition according to the invention advantageously comprises between 0.0001% and 20% by weight of benzoyl peroxide and between 0.0001% and 20% by weight of retinoid relative to the total weight of the composition, and preferably, respectively, between 0.025% and 10% by weight of benzoyl peroxide and between 0.001% and 10% by weight of retinoid relative to the total weight of the composition.

For example, in compositions for treating acne, the benzoyl peroxide is preferably used at concentrations ranging from 2% to 10% by weight and more particularly from 2.5% to 5% by weight, relative to the total weight of the composition. As regards the retinoid, it is used in this type of composition at concentrations generally ranging from 0.05% to 1% by weight relative to the total weight of the composition.

Advantageously, the particle size of the retinoid and of the benzoyl peroxide is such that at least 80% in numerical terms of the particles, and preferably at least 90% in numerical terms of the particles, have a diameter of less than 25 μm and at least 99% in numerical terms of the particles have a diameter of less than 100 μm.

According to the invention, the gel containing benzoyl peroxide and a retinoid advantageously comprises at least water and may also comprise a pro-penetrating agent and/or a liquid wetting surfactant.

The compositions of the invention may contain one or more pro-penetrating agents in preferential concentrations ranging from 0% to 20% and more preferably ranging from 2% to 6% by weight, relative to the total weight of the composition. They should generally not dissolve the active agents at the percentage used, should not cause any exothermic reactions harmful to the benzoyl peroxide, should aid in the satisfactory dispersion of the active agents, and should have antifoaming properties. Among the pro penetrating agents preferably used, without this list being limiting, are compounds such as propylene glycol, dipropylene glycol, propylene glycol dipelargonate, lauroglycol and ethoxydiglycol.

The pro-penetrating agent that is particularly preferred is propylene glycol.

Advantageously, the compositions according to the invention may also contain one or more liquid wetting surfactants in preferential concentrations ranging from 0% to 10% and more preferably ranging from 0.1% to 2%. The wetting power is the tendency of a liquid to spread over a surface.

They are preferably surfactants with an HLB (Hydrophilic-Lipophilic Balance) value from 7 to 9, or nonionic surfactants such as polyoxyethylenated and/or polyoxypropylenated copolymers. They should be liquid so as to be readily incorporated into the composition without it being necessary to heat them.

Among the wetting agents that are preferably used, without this list being limiting, are compounds of the Poloxamer family and more particularly Poloxamer 124 and/or Poloxamer 182.

The liquid wetting surfactant that is particularly preferred is Poloxamer 124.

The composition may also comprise any additive usually used in the cosmetics or pharmaceutical field, such as sequestering agents, antioxidants, sunscreens, preserving agents, fillers, electrolytes, humectants, colorants, common mineral or organic acids or bases, fragrances, essential oils, cosmetic active agents, moisturizers, vitamins, essential fatty acids, sphingolipids, self-tanning compounds such as DHA, and calmants and protective agents for the skin such as allantoin. Needless to say, a person skilled in the art will take care to select this or these optional additional compound(s), and/or the amount thereof, such that the advantageous properties of the composition according to the invention are not, or are not substantially, adversely affected.

These additives may be present in the composition in a proportion of from 0% to 20% by weight relative to the total weight of the composition.

Examples of sequestering agents that may be mentioned include ethylenediaminetetraacetic acid (EDTA), and also derivatives or salts thereof, dihydroxyethylglycine, citric acid and tartaric acid, or mixtures thereof.

Examples of preserving agents that may be mentioned include benzalkonium chloride, phenoxy-ethanol, benzyl alcohol, diazolidinylurea and parabens, or mixtures thereof.

Examples of humectants that may be mentioned include glycerol and sorbitol.

In particular, the invention also relates to a pharmaceutical or cosmetic composition for topical application to the skin, the integuments or mucous membranes, in the form of an aqueous gel, characterized in that it contains, in a physiologically acceptable medium that is compatible with topical application to the skin, the integuments or mucous membranes, an active phase comprising (expressed in percentages by weight):

0% to 90%, preferably 5% to 25% and especially 10% to 20%, of water;

0% to 10%, preferably 0 to 2% and especially 0% to 0.5%, of liquid wetting surfactant;

0% to 20%, preferably 0% to 10% and especially 2% to 5%, of pro-penetrating agent;

0.0001% to 20% and preferably 0.025% to 10%, of benzoyl peroxide;

0.0001% to 20% and preferably 0.001% to 10%, of retinoid; and an aqueous phase comprising a pH-independent gelling agent, and water.

The aqueous phase of the emulsion according to the invention may comprise water, a floral water such as cornflower water, or natural mineral or spring water chosen, for example, from eau de Vittel, waters of the Vichy basin, eau d'Uriage, eau de la Roche Posay, eau de la Bourboule, eau d'Enghien-les-Bains, eau de Saint Gervais-les-Bains, eau de Néris-les-Bains, eau d'Allevard-les-Bains, eau de Digne, eau de Maizières, eau de Neyrac-les-Bains, eau de Lons-le-Saunier, les Eaux Bonnes, eau de Rochefort, eau de Saint Christau, eau des Fumades, eau de Tercis-les-bains, eau d'Avène or eau d'Aix les Bains.

The said aqueous phase may be present in a content of between 10% and 90% by weight and preferably between 20% and 80% by weight, relative to the total weight of the composition.

A composition that is preferred according to the invention comprises in water:
2.50% benzoyl peroxide,
0.10% adapalene,
0.10% disodium EDTA,
4.00% glycerol,
4.00% propylene glycol,
0.05% sodium docusate,
0.20% Poloxamer 124,
4.00% sodium acryloyldimethyltaurate copolymer & isohexadecane & polysorbate 80,
sodium hydroxide, qs pH 5.

A subject of the present invention is also the composition as described above, as a medicinal product.

The invention also relates to the use of the novel composition as described above in cosmetics and dermatology.

A subject of the invention is also a process for preparing a composition of aqueous gel type, comprising the production of an active phase, of an aqueous phase and of a gelling phase, at room temperature (RT), i.e., between 20 and 25° C., and successively comprising the following steps:
a) the preparation of an aqueous phase comprising water and optionally a chelating agent and/or a pro-penetrating agent and/or a humectant;
b) the preparation of an active phase comprising the mixture in water of the retinoid, of benzoyl peroxide and, optionally, of a liquid wetting surfactant and/or of a pro-penetrating agent, with stirring;
c) the introduction of the active phase into the aqueous phase, with stirring; and
d) the introduction of the gelling agent into the mixture obtained from step c), with stirring.

In one embodiment, the process for preparing the aqueous gel composition, comprising the production of an active phase, of an aqueous phase and of a gelling phase, at room temperature, successively comprises the following steps:
a) the preparation of an aqueous phase comprising water and optionally a chelating agent and/or a pro-penetrating agent and/or a humectant;
b) the preparation of two active agents, one comprising the mixture in water of the retinoid, the other comprising the mixture in water of benzoyl peroxide and, optionally, of a liquid wetting surfactant and/or of a pro-penetrating agent, with stirring;
c) the introduction of the active phases into the aqueous phase, with stirring; and
d) the introduction of the galling agent into the mixture obtained from step c), with stirring.

The aqueous gel prepared according to one of these procedures was found to provide many advantages over the preparation of other already-known aqueous gels, especially since it is simpler, and, since the incorporation of the gelling agent into the end of the process makes it possible to obtain better dispersion of the particles by enclosure, these gels may also be film-forming and may thus limit perspiration. At least 80% in numerical terms of the particles and preferably at least 90% in numerical terms of the particles have a diameter of less than 25 µm and at least 99% in numerical terms of the particles have a diameter of less than 100 µm in the composition.

On account of the keratolytic, bactericidal and antiinflammatory activity of benzoyl peroxide and the pronounced activity of retinoids in the fields of cell differentiation and proliferation, the compositions of the invention are particularly suitable in the following therapeutic fields:
1) for treating dermatological complaints associated with a keratinization disorder relating to differentiation and proliferation, especially for treating common acne, comedones, polymorphonuclear leukocytes, acne rosacea, nodulocystic acne, acne conglobata, senile acne, secondary acnes such as solar acne, medication-related acne or occupational acne, and suppurative hydradenitis,
2) for treating other types of keratinization disorder, especially ichtyosis, ichtyosiform conditions, Darier's disease, palmopiantar keratoderma, leukoplakia and leukoplakiform conditions, and cutaneous or mucous (buccal) lichen,
3) for treating other dermatological complaints associated with a keratinization disorder with an inflammatory and/or immunoallergic component, and especially all forms of psoriasis, whether cutaneous, mucous or ungual psoriasis, and even psoriatic rheumatism, or cutaneous atopy, such as eczema, or respiratory atopy, or even gingival hypertrophy; the compounds may also be used in certain inflammatory complaints not exhibiting a keratinization disorder, such as folliculitis,
4) for treating all dermal or epidermal proliferations, whether benign or malignant, and whether of viral origin or otherwise, such as common warts, flat warts, molluscum contagiosum and verruciform epidermodysplasia, oral or florid papillomatoses and proliferations that may be induced by ultraviolet radiation, especially in the case of actinic keratosis,
5) for repairing or combating aging of the skin, whether photo induced or chronological aging, or for reducing pigmentation, or any pathology associated with chronological or actinic aging,
6) for preventively or curatively treating cicatrization disorders and skin ulcers, for preventing or repairing stretch marks, or for promoting cicatrization,
7) for combating sebaceous function disorders such as the hyperseborrhoea of acne or simple seborrhoea,
8) in the treatment of any complaint of fungal origin on the skin, such as tinea pedis and tinea versicolor,
9) in the treatment of dermatological complaints with an immunological component,
10) in the treatment of skin disorders caused by exposure to UV rays, and
11) in the treatment of dermatological complaints associated with inflammation or infection of the tissues surrounding the hair follicles, caused especially by microbial colonization or infection, especially impetigo, seborrhoeic dermatitis, folliculitis or sycosis barbae, or involving any other bacterial or fungal agent.

The compositions according to the invention are particularly suitable for preventively or curatively treating common acne.

A subject of the invention also relates to the manufacture of a pharmaceutical preparation for preventing or treating dermatological complaints associated with cell differentiation and/or proliferation disorders and/or keratinization disorders, and also to the manufacture of a pharmaceutical preparation for preventing or treating common acne.

The compositions according to the invention also find an application in cosmetics, in particular for treating acne-prone skin, for regrowth of the hair, for preventing hair loss, for combating the greasy appearance of the skin or the hair, in protecting against the harmful effects of sunlight or in the treatment of physiologically dry skin, or for preventing and/or combating photo induced or chronological aging.

The compositions according to the invention also find an application in body and hair hygiene.

The present invention thus relates also to the cosmetic use of a composition according to the invention for treating acne-prone skin, for regrowth of the hair or for preventing hair loss, for combating the greasy appearance of the skin or the hair, in protecting against harmful effects of sunlight or in treating physiologically dry skin, or for preventing and/or controlling photo induced or chronological aging.

The formulation examples below illustrate the compositions according to the invention without, however, limiting its scope. Examples of processes for preparing the compositions according to the invention, mentioned in a non-limiting manner, and also examples illustrating the physical and chemical stability of the compositions, are also described.

I. Formulation Examples

In the compositions below (Examples 1 to 5), the proportions of the various constituents are expressed as percentages by weight relative to the total weight of the composition.

Example 1

| Phase | Components | % |
|---|---|---|
| Active | BENZOYL PEROXIDE | 5.00% |
| | ADAPALENE | 0.10% |
| | DIPROPYLENE GLYCOL | 4.00% |
| | PURIFIED WATER | 10% |
| | POLOXAMER 182 | 0.20% |
| Aqueous | PURIFIED WATER | qs 100% |
| | SILICA | 0.02% |
| | GLYCEROL | 2.00% |
| | MICROSPONGES | 4.00% |
| Gelling | POLYACRYLAMIDE (and) C13-14 ISOPARAFFIN (and) LAURETH-7 | 3.50% |

Example 2

| Phase | Components | % |
|---|---|---|
| Active | BENZOYL PEROXIDE | 5% |
| | ADAPALENE | 0.10% |
| | PURIFIED WATER | 10.00% |
| | PROPYLENE GLYCOL | 2.00% |
| | POLOXAMER 124 | 0.20% |
| Aqueous | PURIFIED WATER | qs 100% |
| | DISODIUM EDTA | 0.10% |
| | GLYCEROL | 4.00% |
| | PROPYLENE GLYCOL | 2.00% |
| | SODIUM DOCUSATE | 0.05% |
| Gelling | SODIUM ACRYLOYLDIMETHYLTAURATE COPOLYMER & ISOHEXADECANE & POLYSORBATE 80 | 4.00% |

Example 3

| Phase | Components | % |
|---|---|---|
| Active | BENZOYL PEROXIDE | 2.5% |
| | ADAPALENE | 0.10% |
| | PURIFIED WATER | 10.00% |
| | PROPYLENE GLYCOL | 2.00% |
| | POLOXAMER 124 | 0.20% |
| Aqueous | PURIFIED WATER | qs 100% |
| | DISODIUM EDTA | 0.10% |
| | GLYCEROL | 4.00% |
| | PROPYLENE GLYCOL | 2.00% |
| | SODIUM DOCUSATE | 0.05% |
| Gelling | SODIUM ACRYLOYLDIMETHYLTAURATE COPOLYMER & ISOHEXADECANE & POLYSORBATE 80 | 4.00% |
| pH modifier | SODIUM HYDROXIDE | qs pH 5.00 |

Example 4

| Phase | Components | % |
|---|---|---|
| Active | BENZOYL PEROXIDE | 5.00% |
| | ADAPALENE | 0.10% |
| | PURIFIED WATER | 10.00% |
| | PROPYLENE GLYCOL | 2.00% |
| | POLOXAMER 124 | 0.20% |
| Aqueous | PURIFIED WATER | qs 100% |
| | DISODIUM EDTA | 0.10% |
| | GLYCEROL | 4.00% |
| | PROPYLENE GLYCOL | 2.00% |
| | SODIUM C14-16 OLEFIN SULFONATE | 0.05% |
| Components | PEG-150/decyl/SMDI copolymer | 3.5% |

Example 5

| Phase | Components | % |
|---|---|---|
| Active 1 | BENZOYL PEROXIDE | 2.5% |
| | PURIFIED WATER | 20.00% |
| | PROPYLENE GLYCOL | 1.00% |
| | POLOXAMER 124 | 0.10% |
| Phase | ADAPALENE | 0.10% |
| Active 2 | PROPYLENE GLYCOL | 1.00% |
| | POLOXAMER 124 | 0.10% |
| Aqueous | PURIFIED WATER | qs 100% |
| | DISODIUM EDTA | 0.10% |
| | GLYCEROL | 4.00% |
| | PROPYLENE GLYCOL | 2.00% |
| | SODIUM DOCUSATE | 0.05% |
| Gelling | SODIUM ACRYLOYLDIMETHYLTAURATE COPOLYMER & ISOHEXADECANE & POLYSORBATE 80 | 4.00% |
| pH modifier | SODIUM HYDROXIDE | qs pH 5.00 |

II. Examples of a Preparation Process

Example 6

The examples of a preparation process are given in a non-limiting manner. The preparation presented is that of the composition that is the subject of Example 3:

| PROCEDURE | PARAMETERS |
|---|---|
| Introduce the following into beaker (Phase 1): purified water disodium EDTA glycerol | T°: RT ° C.<br>STIRRER: Rayneri<br>PADDLE: deflocculating<br>STIRRING: 350 rmp<br>TIME: 10 min |
| Introduce the following into a related beaker: propylene glycol sodium docusate Place under magnetic stirring until the sodium docusate is fully dissolved | T°: RT ° C.<br>STIRRER: stirring plate<br>PADDLE: magnetic br<br>TURBOMIXER: N.A.<br>TIME: 45 min |
| Active phase: Introduce the following into a related beaker of suitable size: propylene glycol (PG) Poloxamer 124 purified water benzoyl peroxide adapalene Stir using a Polytron stirrer until the active agents are fully | T°: RT ° C.<br>STIRRER: disperser<br>PADDLE: Polytron<br>STIRRING: 9000 rpm<br>TIME: 30 min |

-continued

| PROCEDURE | PARAMETERS |
|---|---|
| dispersed, in a bath of cold water to avoid overheating of the active agents. | |
| When the mixture of sodium docusate + PG is fully dissolved, incorporate it into Phase 1. Next, add the active phase. Stir with a Rayneri stirrer until a homogeneous mixture is obtained. | T°: RT ° C. STIRRER: Rayneri PADDLE: deflocculating STIRRING: 400-600 rpm TIME: 20 min |
| Finally, add the following: Simulgel 600 Stir with a Rayneri stirrer for the time required for good homogeneity of the finished product. | T°: RT ° C. STIRRER: Rayneri PADDLE: deflocculating STIRRING: 1000-1200 rpm TIME: 25 min |
| Neutralization: Adjust the pH to 5.00 ± 0.3 with: 10% sodium hydroxide, qs | T°: RT ° C. STIRRER: Rayneri PADDLE: deflocculating STIRRING: 1000-1200 rpm TIME: 25 min |

The preparation given is that of the composition that is the subject of Example 5:

| PROCEDURE | PARAMETERS |
|---|---|
| Introduce the following into a beaker: purified water disodium EDTA sodium docusate propylene glycol Place under magnetic stirring until the sodium docusate is fully dissolved | T°: RT ° C. STIRRER: Rayneri PADDLE: deflocculating STIRRING: 350 rpm TIME: 50 min |
| Next, introduce the following glycerol | T°: RT ° C. STIRRER: stirring plate PADDLE: deflocculating STIRRING: 350 rpm TIME: 5 min |
| Active phase 1: Introduce the following into a related beaker of suitable size: propylene glycol (PG) Poloxamer 124 purified water benzoyl peroxide Stir until the active agent is fully dispersed, in a cold water bath to avoid overheating. | T°: RT + cold water bath PADDLE: Ultra-Turrax STIRRING: 13500 rpm TIME: 30 min |
| Active phase 2: Introduce the following into a related beaker of suitable size: propylene glycol (PG) Poloxamer 124 adapalene. | T°: RT + cold water bath PADDLE: UltraTurrax STIRRING: 9500 rpm TIME: 15 min |
| Incorporate the active phase 2 into the aqueous phase. Next, add the active phase 1. Stir using a Rayneri stirrer until a homogeneous mixture is obtained | T°: RT ° C. STIRRER: Rayneri PADDLE: deflocculating STIRRING: 300 rpm TIME: 20 min |
| Finally, add the following: Simulgel 600 Stir using a Rayneri stirrer for the time required for good homogeneity of the finished product | T°: RT ° C. STIRRER: Rayneri PADDLE: deflocculating STIRRING: 680 rpm TIME: 35 min |
| Neutralization: Adjust the pH to 5.00 ± 0.3 with: 10% sodium hydroxide, qs | T°: RT ° C. STIRRER: Rayneri PADDLE: deflocculating STIRRING: 680 rpm TIME: 25 min |

III. Stability Study

Example 6

Physical Stability of the Composition by Measuring the Flow Threshold (in Pa·s$^{-1}$)

The tests performed are viscosity measurements for plotting curves known as rheograms, which make it possible, for a given rate gradient γ, to measure a shear stress τ, and for a given shear stress τ, to measure a rate gradient γ ("Initiation à la rhéologie" [Introduction to rheology] Gouarraze-Grossiord 1991; "La viscosité at as meaure dans les pharmacopées" [Viscosity and its measurement in pharmacopoeias]; L. Molle, Journal Pharma Belg. 1975, 30, 5-6, 597-619).

The term "yield value" means the force required (minimum shear stress) to overcome the cohesion forces of Van der Waals type and to bring about flow.

The yield value (τ0) is extrapolated either visually (γ-axis at the origin of the rheograms) or by calculation (application of mathematical models).

Composition of the Gels Used:

| Aqueous gel based carbomer | |
|---|---|
| Constituents | % |
| PURIFIED WATER | qs 100% |
| DISODIUM EDTA | 0.10 |
| SODIUM DOCUSATE | 0.05 |
| SILICA (AEROSIL 200) | 0.02 |
| HAPROMFR (CARBOPOL 980) | 0.85 |
| GLYCEROL | 4.00 |
| PROPYLENE GLYCOL | 4.00 |
| POLOXAMER 124 | 0.20 |
| BENZOYL PEROXIDE MICROSPONGES | qs 2.5% 8PO |
| ADAPALENE | 0.10 |
| 10% SODIUM HYDROXIDE | 2.00 as pH 5 |

| Aqueous gel based on hydroxypropylcellulose | |
|---|---|
| Constituents | % |
| PURIFIED WATER | qs 100% |
| DISODIUM EDTA | 0.10 |
| SILICA (AEROSIL 200) | 0.02 |
| GLYCEROL | 4.00 |
| CLAY (VEEGUM K) | 2.00 |
| XANTHAN GUM (KELTROL T) | 0.5 |
| HYDROXYPROPYLCELLULOSE (NATROSOL HHX) | 1.5 |
| PROPYLENE GLYCOL | 4.0 |
| SODIUM DOCUSATE | 0.05 |
| POLOXAMER 124 | 0.2 |
| BENZOYL PEROXIDE MICROSPONGES | qs 2.5% BPO |
| ADAPALENE | 0.10 |

| | Example 2 in accordance with the invention | | Aqueous gel based on carbomer | | Aqueous gel based on hydroxypropyl-cellulose and aluminum magnesium silicate | |
|---|---|---|---|---|---|---|
| Temperature | RT | T40° C. | RT | T40° C. | RT | T40° C. |
| T initial | 137 | / | 111 | / | 170 | |
| T 1 month | 139 | 137 | 135 | 111 | 183 | 93 |
| T 2 months | 147 | 121 | / | / | 188 | 65 |
| T 3 months | 149 | 127 | 100 | 76 | 147 | 34 |

RT: room temperature
T40° C.: storage at 40° C.

The yield value of the composition according to the invention is stable over time and with temperature, unlike the other two examples of aqueous gel, whose viscosity falls rapidly over time, both at room temperature and at 40° C. These results demonstrate the vary good physical stability of the composition according to the invention over time, unlike the standard compositions of aqueous gels.

Example 7

Stability of Benzoyl Peroxide Over Time and as a Function of the Storage Temperature by Measuring the Amount of Benzoyl Peroxide in the Composition (in Percentages)

The percentages of benzoyl peroxide (BPO) presented in the table below were obtained by measuring the benzoyl peroxide concentration by iodometry. A suitable amount of composition is first dissolved in purified water and then in acetonitrile, and subjected to the action of a potassium iodide solution. When the potassium iodide is added, a color change from white to brown takes place,
indicating the presence of benzoyl peroxide in the composition. The iodine released is titrated using 0.1N sodium thiosulphate solution:

$$I_2 + 2N_2S_2O_3 \rightarrow 2NaI + Na_2S_4O_5$$

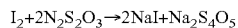

The percentages of benzoyl peroxide given in the table below correspond to the percentage of benzoyl peroxide measured in the product relative to the theoretical amount introduced.

| Temperature | Example 2 in accordance with the invention RT | T40° C. | Aqueous gel based on carbomer RT | T40° C. | Aqueous gel based on hydroxypropyl-cellulose and aluminum magnesium silicate RT | T40° C. |
|---|---|---|---|---|---|---|
| % BPO at T initial | 100 | / | 94.3 | / | 101.7 | |
| % BPO at T 1 month | Not performed | 102.5 | 95.7 | 90.3 | / | 94.9 |
| % BPO at T 2 months | Not performed | 99.1 | 94.3 | 85.5 | / | 87.3 |
| % BPO at T 3 months | 102.4 | 100.3 | 94 | 78.3 | 99.7 | 85.8 |

In the composition of Example 2, the percentage of benzoyl peroxide over time remains stable and equivalent to 100% both at room temperature and at 40° C. The benzoyl peroxide present in the other two examples of prior-art aqueous gels degrades significantly over time. After 3 months, a loss of benzoyl peroxide that is up to 6% at room temperature and at least 14% at T40° C. may be observed. These results demonstrate that the compositions according to the invention allow very good stability of benzoyl peroxide over time, even at 40° C., unlike standard compositions.

What is claimed is:

1. A physiologically acceptable aqueous gel composition for treatment of common acne comprising:
    (1) anti-acne actives consisting of:
        0.05% to 1 adapalene and/or at least one pharmaceutically acceptable salt thereof, and
        2.5% to 5% dispersed benzoyl peroxide; and
    (2) 2% to 5% acrylamide sodium acryloyldimethyltaurate/isohexadecane/polysorbate 80 gelling agent, said percentages being based on the weight of the total aqueous gel composition for treatment of common acne.

2. A method for treating common acne comprising administering, to a subject in need thereof, a physiologically acceptable aqueous gel composition for treatment of common acne comprising:
    (1) anti-acne actives consisting of
        0.05% to 1% adapalene and/or at least one pharmaceutically acceptable salt thereof, and
        2.5% to 5% dispersed benzoyl peroxide; and
    (2) 2% to 5% acrylamide sodium acryloyldimethyltaurate/isohexadecane/polysorbate 80 gelling agent, said percentages being based on the weight of the total aqueous gel composition for treatment of common acne.

3. A product for treatment of common acne comprising:
a container; and
a physiologically acceptable aqueous gel composition for treatment of common acne comprising:
    (1) anti-acne actives consisting of:
        0.05% to 1% adapalene and/or at least one pharmaceutically acceptable salt thereof, and
        2.5% to 5% dispersed benzoyl peroxide; and
    (2) 2% to 5% acrylamide sodium acryloyldimethyltaurate/isohexadecane/polysorbate 80 gelling agent, said percentages being based on the weight of the total aqueous gel composition for treatment of common acne,
wherein the container contains the aqueous gel composition.

* * * * *

UNITED STATES PATENT AND TRADEMARK OFFICE
CERTIFICATE OF CORRECTION

| | | |
|---|---|---|
| PATENT NO. | : 8,936,800 B2 | Page 1 of 1 |
| APPLICATION NO. | : 13/660831 | |
| DATED | : January 20, 2015 | |
| INVENTOR(S) | : Sandrine Orsoni and Nathalie Willcox | |

It is certified that error appears in the above-identified patent and that said Letters Patent is hereby corrected as shown below:

In the Claims

In claim 1, column 14, line 14, after "1", insert -- % --.

Signed and Sealed this
Fifth Day of May, 2015

Michelle K. Lee
*Director of the United States Patent and Trademark Office*